United States Patent [19]

Kramer et al.

[11] Patent Number: 4,789,638

[45] Date of Patent: Dec. 6, 1988

[54] PROCESS AND APPARATUS FOR THE DETECTION OF HYDRAZINE AND HYDRAZINE DERIVATIVES

[76] Inventors: David N. Kramer, 2119 Wiltonwood Rd., Stevenson, Md. 21153; Philip A. Snow, Box 53, Bee Tree Rd., Henderson, Md. 21640

[21] Appl. No.: 46,385

[22] Filed: May 6, 1987

[51] Int. Cl.$^4$ .................. G01N 22/00; G01N 1/48; G01N 33/00; G01N 21/77
[52] U.S. Cl. .................. 436/111; 422/55; 422/60; 422/83; 436/169
[58] Field of Search .................. 436/106.9, 124, 111, 436/112, 164, 165, 169, 170; 422/58, 86, 83, 59, 60

[56] References Cited

U.S. PATENT DOCUMENTS 3,025,142 3/1962 Williams .................. 422/60
4,230,457 10/1980 Leichnitz .................. 422/60

OTHER PUBLICATIONS

Iodometric Microdetermination of Hydrazines by Amplification Reaction, Talanta, vol. 22, pp. 757-760, 1975.

*Primary Examiner*—Barry S. Richman
*Assistant Examiner*—Lyle Alfandary Alexander
*Attorney, Agent, or Firm*—Leonard Bloom

[57] ABSTRACT

Process and apparatus for the detection of hydrazine and hydrazine derivatives. For the detection of hydrazine and volatile hydrazine derivatives in air, preferred is a detector tube having iodate or periodate ion in a reactor zone and an iodine sensitive colorimetric indicator in a separate indicator zone. The colorimetric indicator may be an addition-complex type indicator, a redox sensitive dye precursor or an iodination type dye precursor. The hydrazine or hydrazine derivative contacts the iodate or periodate ion in the reactor zone to form iodine which diffuses or is drawn into the indicator zone where it contacts the indicator which then undergoes a color change. In a particularly preferred embodiment of the detector tube, an oxidizing metal ion is present in the reactor zone and, when a redox sensitive indicator is employed, in the indicator zone. The oxidizing metal ion in the reactor zone reacts with excess iodide ion to prevent its reaction with iodine to form the nonvolatile triiodide ion which, if formed, precludes diffusion of iodine into the indicator portion of the detector tube. The oxidizing metal ion in the indicator zone oxidizes iodide ion, formed as a result of the reaction of iodine with a redox sensitive indicator, back to iodine. The iodine thus formed is free to react with more of the indicator, thus enhancing sensitivity.

44 Claims, 2 Drawing Sheets

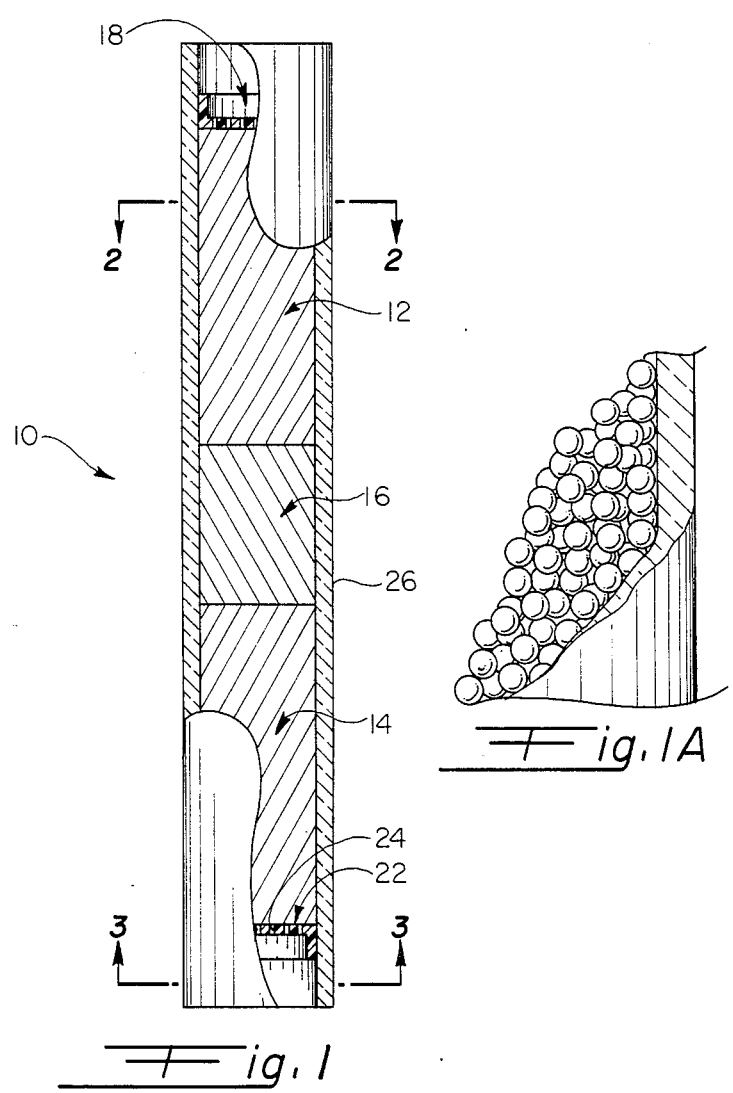
Fig. 1
Fig. 1A
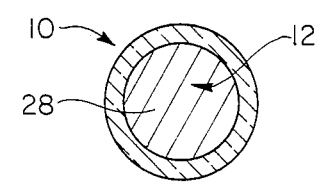
Fig. 2
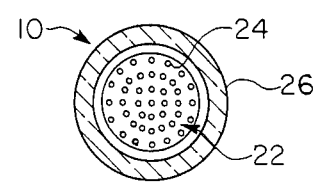
Fig. 3

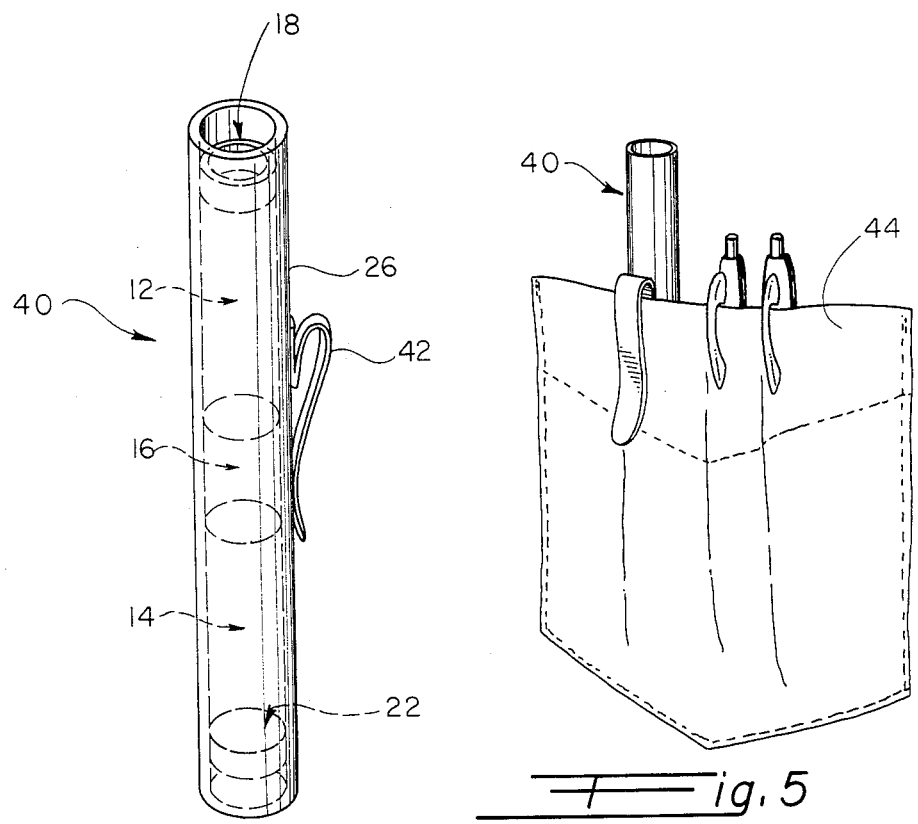
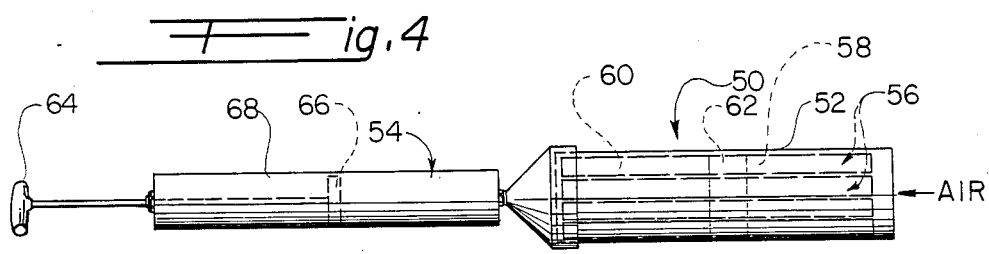
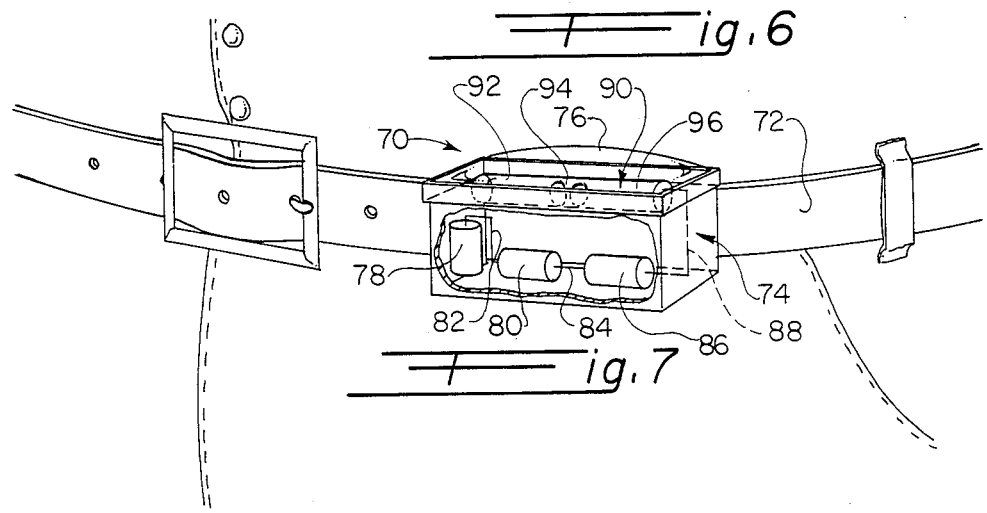

PROCESS AND APPARATUS FOR THE DETECTION OF HYDRAZINE AND HYDRAZINE DERIVATIVES

FIELD OF THE INVENTION

This invention provides method and apparatus for the colorimetric detection of hydrazine and hydrazine derivatives.

BACKGROUND OF THE INVENTION

There is a continual need to detect hydrazine and hydrazine derivatives. There is an OSHA requirement to prevent exposure to hydrazine and its derivatives at concentrations greater than one part per million (1.3 mg/m$^3$). TWA (time weighted average for 8 hours). Hydrazine and hydrazine derivatives are combustibly strong reducing agents that react violently with oxidizing agents and thus present a safety hazard. Hydrazine and hydrazine derivatives are well known components of liquid rocket fuels in conjunction with an oxidizing agent such as an oxide of nitrogen, e.g., $N_2O_4$. Thus, at facilities where liquid-fueled rockets are prepared for flight, there is a need to provide reliable and sensitive monitoring devices and procedures to determine if hydrazine or hydrazine derivatives have been introduced into the workplace.

It is known in the art that hydrazine and its derivatives may be analyzed with iodate ion, which is reduced to iodine by the hydrazine or hydrazine derivative, and the iodine is then detected with an addition-complex type indicator such as starch or an iodination type dye precursor such as fluorescein. This procedure is deficient in that hydrazine or hydrazine derivative reacts with iodine to reduce it to iodide ion, thus reducing the sensitivity of the test.

Also known in the prior art is a detector tube device invented by Draeger which is used to detect the presence of hydrazine and volatile hydrazine derivatives in air. There are two embodiments of the Draeger device: a passive detector tube and a detector tube fitted with a hand piston pump to draw the hydrazine-laden air through the reagents. The Draeger device, whether it be the passive detector tube or the detector tube fitted with a hand piston pump, is adapted to use either one of two detecting reagent systems. One detecting reagent is the pH indicator p-bromphenol blue which changes from yellow to blue in the pH range of 3.0-4.6. The yellow acid form of the indicator is converted to the blue alkaline form by reaction with hydrazine. This reaction, however, is not specific for hydrazine since any alkaline amine or ammonia, which are usually present in emissions from hydrazine rocket fuels, will produce an identical response with p-bromphenol blue. Also, the presence of acidic volatiles will desensitize the detecting reagent.

A later modification of the Draeger hydrazine detector employs as the detecting reagent a silver salt which, upon reaction with hydrazine, is reduced to the grey-black metallic silver. A serious drawback of this detecting reagent is the expense of silver salts.

SUMMARY OF THE INVENTION

The process and apparatus of this invention overcome the deficiencies of the prior art. In the instant invention, hydrazine or a hydrazine derivative is contacted with readily available and inexpensive iodate or periodate ion in the presence of an oxidizing metal ion such as ferric or cupric ion. Using iodate as the example, the hydrazine or hydrazine derivative reduces iodate ion to iodide ion which then reacts with excess iodate ion to form iodine. The iodine is detected colorimetrically with an iodine sensitive colorimetric indicator such as an addition-complex type or an iodination type dye precursor. A redox sensitive indicator cannot be used in the presence of iodate ion or periodate ion. Iodine is reduced to iodide ion by hydrazine or hydrazine derivative. The iodide ion reacts with the oxidizing metal ion and is oxidized back to iodine which reacts with more indicator. The sensitivity of the test is thus markedly enhanced. By the foregoing method, hydrazine and hydrazine derivatives may be detected in solution as well as in air.

Hydrazine and volatile hydrazine derivatives in air may be detected with the use of films or badges impregnated with iodate or periodate ion, oxidizing metal ion and a suitable indicator for iodine. Preferred is a detector tube device of either the passive or the piston type having iodate or periodate ion in a reactor zone and an iodine sensitive colorimetric indicator in a separate indicator zone. A redox sensitive dye precursor may be used as the indicator in this embodiment of the invention. The hydrazine or hydrazine derivative contacts the iodate or periodate ion in the reactor zone to form iodide ion which reacts with excess iodate or periodate ion to form iodine which diffuses or is drawn into the indicator zone where it contacts the iodine sensitive indicator, which then undergoes a color change. In a particularly preferred embodiment of the detector tube device, an oxidizing metal ion is present in the reactor zone and in the indicator zone. The oxidizing metal ion in the reactor zone reacts with excess iodide ion to prevent its reaction with iodine to form the non-volatile triiodide ion which, if formed, precludes diffusion of iodine into the indicator portion of the detector tube. The oxidizing metal ion in the indicator zone oxidizes iodide ion, formed as a result of the reaction of iodine with a redox sensitive indicator, back to iodine. The iodine thus formed is free to react with more of the indicator, thus enhancing sensitivity.

It is therefore an object of this invention to provide process and apparatus for the economical detection of hydrazine and hydrazine derivatives.

It is another object of this invention to provide a sensitive process for the colorimetric detection of hydrazine and It is yet another object of this invention to provide a device for the colorimetric detection of hydrazine and volatile hydrazine compounds in air.

It is still another object of this invention to provide both a personal and an area monitor for the detection of hydrazine and its volatile derivatives in air.

Still other objects will be apparent to those skilled in the art.

The foregoing and other objects are accomplished by the practice of this invention. Broadly, viewed in one of its principal aspects, this invention consists of a process for the colorimetric detection of hydrazine and hydrazine derivatives comprising the step of contacting the sample containing said hydrazine or hydrazine compound with an ion selected from the group consisting of iodate ion and periodate ion, an oxidizing metal ion and a suitable colorimetric indicator for iodine.

A preferred embodiment of the process, for the colorimetric detection of hydrazine and volatile hydrazine derivatives in air, comprises the steps of (1) bringing air containing said hydrazine or volatile hydrazine derivative into a reactor zone containing an ion selected from the group consisting of iodate ion and periodate ion to thereby form iodine and (2) allowing said iodine to move from said reactor zone to an indicator zone containing an indicator which changes color in the presence of iodine.

The foregoing process for the colorimetric detection of hydrazine or volatile hydrazine derivative in air is carried out in a detector tube device comprising a reactor zone and an indicator zone, said reactor zone and said indicator zone being open to the atmosphere, and wherein said reactor zone contains a reagent comprising an ion selected from the group consisting of iodate ion and periodate ion, and wherein said indicator zone is at least partially transparent and contains a colorimetric indicator for iodine.

The instant invention thus broadly provides process and apparatus for the detection of hydrazine and hydrazine derivatives. The invention is characterized by high sensitivity, particularly for the detection of hydrazine and volatile hydrazine derivatives in air. The sample containing hydrazine or hydrazine derivative is brought into contact with iodate ion or periodate ion and an oxidizing metal ion to form iodine. A suitable colorimetric indicator is present to detect the iodine. When iodine reacts with hydrazine or a hydrazine derivative, it is reduced to iodide ion. The oxidizing metal ion oxidizes the iodide ion back to iodine which then reacts with more indicator. The sensitivity of the test is thereby enhanced, with the cycle continuing until the oxidizing metal ion or the indicator is exhausted.

Hydrazine and volatile hydrazine derivatives in pair are preferably detected by means of a detector tube having a reactor zone containing iodate or periodate ion, and an indicator zone containing a colorimetric indicator for iodine. Hydrazine or hydrazine derivative reacts with iodate or periodate ion to form iodide ion which reacts with excess iodate or periodate ion to form iodine. The iodine diffuses or is drawn into the indicator zone of the detector tube where it comes into contact with the indicator which undergoes a color change in its presence. It is preferred that an oxidizing metal ion be present in the reactor zone and the indicator zone.

The nature and substance of the present invention as well as its objects and advantages will be more clearly perceived and fully understood by referring to the following description and claims taken in connection with the accompanying drawings which are described briefly below.

BRIEF DESCRIPTION OF THE DRAWINGS

FIG. 1 is a front elevation of a passive detector tube for the detection of hydrazine and volatile hydrazine derivatives in air with certain parts broken away and sectioned to illustrate three respective zones.

FIG. 1A is a portion of one of the zones of FIG. 1, drawn to an enlarged scale, and showing a plurality of close-packed glass beads used in a preferred embodiment of the invention.

FIG. 2 is a horizontal section through the detector tube of FIG. 1 along line 2—2.

FIG. 3 is a horizontal section through the detector tube of FIG. 1 along line 3—3.

FIG. 4 is a perspective view in section of a passive detector tube for the detection of hydrazine and volatile hydrazine derivatives in air.

FIG. 5 depicts a passive detector tube for the detection of hydrazine and volatile hydrazine derivatives in air clipped to the inside of a shirt pocket.

FIG. 6 is a front elevation of a detector tube device for the detection of hydrazine and volatile hydrazine derivatives in air wherein the air is moved sequentially through a plurality of detector tubes by means of a hand piston pump fitted thereto.

FIG. 7 is a front elevation of a motorized pump driven detector tube device for the detection of hydrazine and volatile hydrazine derivatives in air with certain parts broken away.

DESCRIPTION OF THE PREFERRED EMBODIMENTS

The process of this invention for the detection of hydrazine and hydrazine derivatives is characterized by the use of inexpensive, readily available reagents and by high sensitivity, particularly as it applies to the detection of hydrazine and volatile hydrazine derivatives in air. The process comprises contacting a sample containing hydrazine or a hydrazine derivative with iodate ion or periodate ion, an oxidizing metal ion and a suitable colorimetric indicator for iodine. When hydrazine or a hydrazine derivative is brought into contact with iodate ion or periodate ion, the iodate or periodate ion is reduced to iodide ion. At least a portion of the iodide ion reacts with excess iodate ion or periodate ion, resulting in the formation of iodine. Iodine generation rates are enhanced by maintaining an acidic environment with, for example, boric acid or phosphoric acid. The iodine is detected colorimetrically with an iodine sensitive colorimetric indicator such as an addition-complex type or an iodination type dye precursor. A redox sensitive dye precursor cannot be used in the presence of iodate ion or periodate ion. Hydrazine or hydrazine derivatives react with iodine to reduce it to iodide ion. The oxidizing metal ion then oxidizes the iodide ion back to iodine which may react with indicator. The sensitivity of the test is thus enhanced since the cycle continues until indicator or oxidizing metal ion is exhausted.

The process of this invention finds particular utility in the detection of hydrazine and volatile hydrazine derivatives in air. The detection of hydrazine and volatile hydrazine derivatives in air is carried out in a detector tube device having a reactor zone containing iodate ion or periodate ion and, preferably, an oxidizing metal ion, and an indicator zone containing a colorimetric indicator for iodine and, preferably, also an oxidizing metal ion. In this embodiment of the invention, the indicator may be an addition-complex type, an iodination type dye precursor, or a redox sensitive dye precursor. The oxidizing metal ion in the reactor zone of the detector tube reacts with excess iodide ion to thereby prevent its reaction with iodine to form non-volatile triiodide ion in the reactor zone of the detector tube. Volatile iodine may thus pass from the reactor zone to the indicator zone of the detector tube where it comes into contact with the indicator and is colorimetrically while, in the case of a redox sensitive indicator, being reduced to iodide ion. The oxidizing metal ion, when present in the indicator zone, thus oxidizes the iodide ion back to iodine which reacts with additional indicator, thereby increasing the sensitivity of the test.

Thus, when hydrazine and its derivatives react, for example, with iodate ion in the reactor zone of the detector tube, the latter is reduced to iodide ion. A portion of the iodide ion reacts with excess iodate ion to form volatile iodide which then reacts with residual iodide ion to form the non-volatile triiodide ion. The kinetics favor the reaction of iodide ion and iodine to form triiodide ion rather than the reaction of iodide ion and iodate ion to form iodine. Accordingly, there is little tendency to form volatile iodine in the reactor zone of the detector tube, and the non-volatile triiodide ion which is the favored product cannot migrate from the reactor zone to the indicator zone of the detector tube. Also, hydrazine reacts rapidly with iodine and triiodide ion to form iodide ion. The sensitivity of the test is thus markedly reduced.

A number of competing reactions occur in the reactor zone of the detector tube. The reactions and their relative rates (the lower the number, the more rapid the reaction) are as follows:

|  | Rate |
|---|---|
| hydrazine + iodate ion → iodide ion | 3 |
| iodide ion + iodate ion → iodine | 2 |
| iodine + iodide ion → triiodide ion | 1 |
| hydrazine + iodine → iodide ion | 2 |
| hydrazine + triiodide ion → iodide ion | 2 |

It is apparent from the above that it would be advantageous to convert iodide ion to iodine while avoiding the reaction of iodine with iodide ion to form the non-volatile triiodide ion. This is achieved by the presence in the reactor zone of an oxidizing metal ion such as cupric ion or ferric ion. The oxidizing metal ion reacts with iodide ion in a redox reaction to form iodine. The reactions of cupric ion and ferric ion with iodide ion are as follows:

$$Cu^{++} + 2I^- \rightarrow CuI_2 \quad (1)$$

$$2CuI_2 \rightarrow 2CuI + I_2 \quad (2)$$

$$Fe^{+++} + 3I^- \rightarrow FeI_3 \quad (3)$$

$$2FeI_3 \rightarrow 2FeI_2 + I_2. \quad (4)$$

Competing with the above is the reaction of hydrazine with cupric ion and ferric ion to reduce them to cuprous ion and ferrous ion, respectively:

$$\text{hydrazine} + \text{cupric ion} \rightarrow \text{cuprous ion} \quad (5)$$

$$\text{hydrazine} + \text{ferric ion} \rightarrow \text{ferrous ion}. \quad (6)$$

Offsetting the above is the reaction of iodate ion with cuprous ion and ferrous ion to oxidize them back to cupric ion and ferric ion, respectively:

$$\text{iodate ion} + \text{cuprous ion} \rightarrow \text{cupric ion} + \text{iodide ion} \quad (7)$$

$$\text{iodate ion} + \text{ferrous ion} \rightarrow \text{ferric ion} + \text{iodide ion}. \quad (8)$$

In view of the foregoing reactions, it is apparent that it is advantageous to have present in the reactor zone an excess of; iodate ion and an excess of oxidizing metal ion relative to hydrazine or hydrazine derivative.

It is also advantageous to have an oxidizing metal ion present in the indicator zone of the detector tube. When iodine reacts with a redox sensitive colorimetric indicator in the indicator zone, it is reduced to iodide ion. If an oxidizing metal ion is present, the iodide ion is oxidized back to iodine as is illustrated in equations (1), (2), (3) and (4). This iodine is free to react with more indicator, resulting in increased sensitivity.

The instant invention may be used to detect unsubstituted hydrazine as well as substituted hydrazine derivatives. The substituted hydrazine derivatives may have a hydrocarbyl group on either or both nitrogens. Examples of substituted hydrazine compounds are methylhydrazine, symmetrical dimethylhydrazine, unsymmetrical dimethylhydrazine, ethylhydrazine, symmetrical di-n-propylhydrazine and phenylhydrazine.

Preferred sources of iodate and periodate ion are iodate and periodate salts of the alkali metals and alkaline earth metals. Examples of suitable iodate and periodate salts are sodium iodate, potassium iodate, calcium iodate, barium iodate, magnesium iodate, sodium periodate, potassium periodate, calcium periodate, barium periodate, magnesium periodate and mixtures thereof.

The oxidizing metal ion which reacts with iodide ion is preferably cupric ion or ferric ion. In the practice of this invention, either cupric ion, ferric ion or a combination thereof may be used. Examples of suitable cupric and ferric compounds are cupric sulfate, cupric chloride, ferric sulfate, ferric chloride and mixtures thereof Thus, it may be appreciated that mixtures of the oxidizing metals may be used.

It is particularly preferred to combine the iodate or periodate ions with the oxidizing metal ions. Thus, especially preferred as the source of these ions in the practice of this invention are cupric iodate, cupric periodate, ferric iodate, ferric periodate and mixtures thereof.

The oxidizing metal ion, e.g., cupric ion and ferric ion, thus plays two roles in the practice of this invention. The oxidizing metal ion reacts with iodide ion formed in the reaction of iodine with a redox sensitive colorimetric indicator, oxidizing the iodide ion back to iodine which is then free to react with more indicator. The sensitivity of the test is thus enhanced. In the case where hydrazine and volatile hydrazine derivatives in air are to be detected by means of a detector tube device, the oxidizing metal ion present in the reactor zone of the detector tube enhances the sensitivity of the test. By reacting with iodide ion in the reactor zone of the detector tube, the oxidizing metal ion not only converts the iodide ion to iodine but, by removing iodide ion, formation of the non-volatile triiodide ion is prevented. Volatile iodine formed on the reactor zone of the detector tube may thus pass into the indicator zone, thereby enhancing sensitivity.

Three general types of colorimetric indicator iodine are useful in the practice of this invention. They are the addition-complex type, redox sensitive dye precursors and iodination type dye precursors. Redox sensitive indicators may not be used in the presence of iodate ion or periodate ion. An example of a suitable iodination type dye precursor is dihydrofluorescein, a white non-fluorescent solid. In the presence of iodine, dihydrofluorescein is oxidized to the greenish yellow, fluorescent fluorescein. A suitable redox sensitive indicator is p-phenylenediamine, a colorless compound that is oxidized by iodine to quinoidal blue-green Wurster's salt:

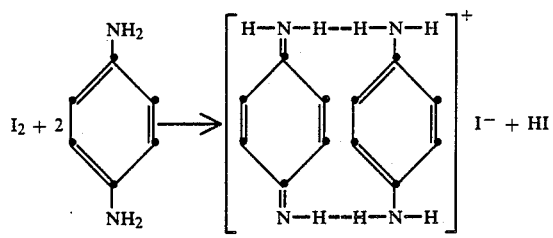

Yet another suitable indicator, though not a redox sensitive indicator, is soluble starch which, in the presence of iodine, forms an intense blue colored addition-complex. Other addition-complex indicators are dextrin and amylose. Also, o-tolidine reacts with iodine to form an unstable meriquinone dye that decomposes after several hours. Detector tube devices using o-tolidine and similar indicators that form unstable dyes thus lend themselves for use in reusable detector tube devices.

The quantities of the reagents used in the practice of this invention and their relative proportions are not critical, but are preferably adjusted to meet sensitivity requirements. In the case of films, badges and the detector tube devices, the reagents may be on a supporting medium. For example, filter paper may be impregnated with the reagents and placed in a mounting to form a badge, or the reagents may be coated on a support such as glass beads, silica gel, pulverized fire brick, molecular sieves, or polymeric granules such as polyethylene granules. The reagents may also be compounded into a polymeric film. Hydrazine and hydrazine derivatives may also be detected by introducing the test sample into a solution such as an aqueous solution containing iodate or periodate ion, oxidizing metal ion, soluble starch and, preferably, a slightly acid buffer.

This invention will be most clearly perceived and best understood through reference to the embodiments discussed in further detail in connection with the drawings. FIG. 1 is a front elevation of a passive detector tube 10 for the detection of hydrazine and volatile hydrazine derivatives in air with certain parts broken away. Detector tube 10 is divided into a reactor zone 12 and an indicator zone 14 separated by an iodine-permeable barrier 16. Barrier 16 may, for example, be a fine mesh or it may be an inert particulate material. The top of detector tube 10 is closed with a plug 18 which contains a plurality of holes 20 through which air containing hydrazine or a volatile hydrazine derivative may enter reactor zone 12. Similarly, the bottom of detector tube 10 is sealed with a plug 22 which contains a plurality of holes 24 which permit the free flow of air containing hydrazine or volatile hydrazine derivatives through detector tube 10. If desired, the outer shell 26 of detector tube 10 may also contain openings. Reactor zone 12 of detector tube 10 contains reagents 28 comprising iodate ion, periodate ion or a mixture thereof and, preferably, an acid buffer and an oxidizing metal ion. These reagents may be present as a mixture of the reactive compounds, e.g., potassium iodate, cupric chloride and boric acid. However, it is preferred that the reagents be on a solid support. For example, filter paper may be impregnated with the reagents or the reagents may, as shown, be coated onto a particulate support such as glass beads, silica gel, pulverized fire brick, a molecular sieve or polyethylene granules. FIG. 1A depicts a portion of one of the zones of FIG. 1, drawn to an enlarged scale, and showing a plurality of close-packed glass beads coated with reagents as used in a preferred embodiment or, alternatively, the reagents themselves.

Indicator zone 14 of detector tube 10 contains reagents 30 comprising a colorimetric indicator for iodine and, preferably, an oxidizing metal ion. It is critical that at least a part of outer shell 26 in the area of indicator zone 14 of detector tube 10 be transparent so that a color change due to the presence of iodine can be observed. It is preferred that the outer shell 26 of detector tube 10 be made entirely of a transparent material such as glass or clear polystyrene. As is the case with the reagents 28 in reactor zone 12, it is preferred that reagents 30 in indicator zone 14 be on a solid support such as filter paper or, as shown, on a particulate support such as glass beads, silica gel, pulverized fire brick, a molecular sieve or polymeric granules.

In practice, air containing hydrazine or a volatile hydrazine derivative enters reactor zone 12 of detector tube 10 through openings 20. Hydrazine or hydrazine derivative reduces iodate or periodate ion to iodide ion which reacts with excess iodate or periodate ion and, if present, with oxidizing metal ion, to yield iodine. The volatile iodine passively diffuses or is drawn through barrier 16 into indicator zone 14 where it reacts with the indicator, which undergoes a color change and, in the case of a redox sensitive indicator, becomes reduced to iodide ion. If, as is preferred, an oxidizing metal ion is present in indicator zone 14, it oxidizes the iodide ion back to iodine which reacts with more indicator. The sensitivity of the test is thus enhanced.

FIG. 2 is a horizontal section through reactor zone 12 of the detector tube 10 of FIG. 1 along line 2—2. The sectional view shows reagents 28 contained within outer shell 26 of detector tube 10.

FIG. 3 is a horizontal section through plug 22 of the detector tube 10 of FIG. 1 along line 3—3. The view depicts the holes 24 in plug 22 which permit air containing hydrazine or volatile hydrazine derivative to pass freely through detector tube 10.

FIG. 4 is a perspective view in section of an embodiment of a passive detector tube 40 for the detection of hydrazine and volatile hydrazine derivatives in air. Detector tube 40 differs from detector tube 10 of FIG. 1 in that a clip 42 is fixed to the outer shell 26 of detector tube 40. All parts of detector tube 40 that are the same as those in detector tube 10 have the same numerical part designations. Detector tube 40 functions identically to detector tube 10 except that it has a lip 42 which is adapted to anchor detector tube 40 to, for example, the fabric of a shirt pocket. While it is preferred that reactor zone 12 be on top and indicator zone 14 on the bottom, if desired the zones could be reversed with reactor zone 12 on the bottom and indicator zone 14 on top. In the embodiment of FIG. 4 it is preferred that the reactor zone 12 be on the top since it is more open to the hydrazine-containing air than is the bottom of detector tube 40, which is inside a shirt pocket when in use.

FIG. 5 depicts the passive detector tube 40 of FIG. 4 clipped to the inside of a shirt pocket 44. The detector tube 40 is thus adapted to be worn by a worker in an environment where there is a danger of the presence of vapors of hydrazine or volatile hydrazine derivatives.

FIG. 6 is a front elevation of a detector tube device 50 for the detection of hydrazine and volatile hydrazine derivatives in air wherein the air is moved sequentially through a plurality of detector tubes by means of a hand piston pump fitted thereto. Detector tube device 50 has at one end a transparent housing 52 which is open at one end to allow for the entry of air and which is attached at its other end to hand piston pump 54. Disposed within housing 52 is a plurality of detector tubes 56 similar to detector tube 10, each of which has a transparent outer shell and each of which may be sequentially rotated into an operative position. Each detector tube 56 has a reactor zone 58, an indicator zone 60 and an iodine-permeable barrier 62. Both ends of detector tubes 56 are sealed with plugs having a plurality of holes to allow the passage of air therethrough.

Pull-handle 64 is attached to piston 66 which is adapted to reciprocate within shell 68 of hand piston pump 54. As piston 66 reciprocates within shell 68 of hand piston pump 54, air is drawn into the reactor zone 58 of a detector tube 56 which is in operative position with pump 54. Hydrazine or volatile hydrazine derivatives in the air react with the reagents in reactor zone 58 to form iodine. Iodine is moved by the air through barrier 62 into indicator zone 60 where it reacts with a colorimetric indicator to produce a color change. When the reagents in a detector tube become exhausted, the next detector tube is rotated into operative position whereby operation of piston pump 54 causes air to be drawn into its reactor zone 58.

FIG. 7 is a front elevation of a motorized pump driven detector tube device 70 for the detection of hydrazine and volatile hydrazine derivatives in air with certain parts broken away. Detector tube device 70 is portable and adapted to be worn on the belt 72 of a person in an area where there is a danger that vapors of hydrazine or hydrazine derivatives may be in the air.

Detector tube device 70 has an outer housing 74 adapted to be removably attached to a belt 72. The top of housing 74 is a transparent window 76 which is preferably a magnifying window. Window 76 may, if desired, be removable from housing 74.

Inside housing 74 is a battery 78 which is connected to electric motor 80 by wires 82. Shaft 84 from motor 80 transmits power to exhaust pump 86. The intake of exhaust pump 86 is connected by tube 88 to indicator zone 96 of detector tube 90 which is essentially the same as detector tube 10 described above in connection with FIG. 1. As exhaust pump 86 operates, it draws air into reactor zone 92 of detector tube 90. Any hydrazine vapor or hydrazine derivative vapor in the air reacts with reagents in reactor zone 92 to form iodine. Iodine is drawn through iodine-permeable barrier 94 and into indicator zone 96 where it reacts with a colorimetric indicator to produce a color change. The color change is observed through transparent window 76.

Thus, the instant invention provides process and apparatus for the detection of hydrazine and hydrazine derivatives. The invention is characterized by high sensitivity, particularly for the detection of hydrazine and volatile hydrazine derivatives in air. The sample containing hydrazine or hydrazine derivative is brought into contact with iodate ion or periodate ion and, preferably, an oxidizing metal ion, to form iodine. A colorimetric indicator for iodine such as an addition-complex type or an iodination type dye precursor is present to detect the iodine. A redox sensitive dye precursor cannot be used in the presence of iodate ion or periodate ion. When iodine reacts with hydrazine or a hydrazine derivative, it is reduced to iodide ion. The oxidizing metal ion, if present, oxidizes the iodide ion back to iodine which reacts with more indicator. The sensitivity of the test is thereby enhanced with the cycle continuing until the oxidizing metal ion or the indicator is exhausted.

Hydrazine and volatile hydrazine derivatives in air are detected by means of a detector tube having a reactor zone containing iodate or periodate ion and an indicator zone containing a colorimetric indicator for iodine. A redox sensitive dye precursor may be used as the indicator in this embodiment of the invention as well as an addition-complex type indicator or an iodination type dye precursor. Preferably, an oxidizing metal ion is also present in the reactor zone and the indicator zone. Iodine formed in the reactor zone by the reaction of hydrazine or volatile hydrazine derivative on the iodate or periodate ion diffuses or is drawn into the indicator zone of the detector tube where it comes into contact with the indicator which undergoes a color change in the presence of iodine. As discussed above, the presence of an oxidizing metal ion in the indicator zone when a redox sensitive indicator is used and in the reactor zone increases the sensitivity of the test.

While specific embodiments of the present invention have been shown and described in detail to illustrate the utilization of the inventive principles, it is to be understood that such showing and description have been offered only by way of example and not by way of limitation. Protection by Letters Patent of this invention in all its aspects as the same are set forth in the appended claims is sought to the broadest extent that the prior art allows.

What is claimed is:

1. A process for the colorimetric detection of hydrazine and hydrazine derivatives in an air sample comprising the step of contacting the sample containing said hydrazine or hydrazine derivative with an ion selected from the group consisting of iodate ion and periodate ion, an oxidizing metal ion and a colorimetric indicator for iodine selected from the group consisting of addition-complex type indicators and iodination type dye precursors.

2. The process of claim 1, wherein the sample containing hydrazine or hydrazine derivative is contacted with an aqueous solution of an ion selected from the group consisting of iodate ion and periodate ion, an oxidizing metal ion and said colorimetric indicator for iodine.

3. A process for the colorimetric detection of hydrazine and volatile hydrazine derivatives in air comprising the step of bringing air containing said hydrazine or volatile hydrazine derivative into contact with a solid support containing an ion selected from the group consisting of iodate ion and periodate ion, an oxidizing metal ion and a colorimetric indicator for iodine selected from the group consisting of addition-complex type indicators and iodination type dye precursors.

4. A process for the colorimetric detection of hydrazine and volatile hydrazine derivatives in air comprising the step of (1) bringing air containing said hydrazine or volatile hydrazine derivative into a reactor zone containing an ion selected from the group consisting of iodate ion and periodate ion to thereby form iodine and (2) allowing said iodine to diffuse from said reactor zone to an indicator zone containing a colorimetric indicator which changes color in the presence of iodine said indicator zone further comprising an oxidizing metal ion.

5. A process for the colorimetric detection of hydrazine and volatile hydrazine derivatives in air comprising the steps of (1) bringing air containing said hydrazine or volatile hydrazine derivative into a reactor zone containing an ion selected from the group consisting of iodate ion and periodate ion to thereby form iodine and (2) allowing said iodine to diffuse from said reactor zone to an indicator zone containing a colorimetric indicator which visibly changes color in the presence of iodine said reactor zone further comprising an oxidizing metal ion.

6. The process of claim 5, said indicator zone further comprising an oxidizing metal ion.

7. The process of claim 6, said reactor zone further comprising a slightly acid buffer.

8. The process of claim 7, wherein said slightly acid buffer is boric acid.

9. The process of claim 8, wherein said oxidizing metal ion is selected from the group consisting of cupric ion, ferric ion and mixtures thereof.

10. The process of claim 9, wherein said colorimetric indicator for iodine is selected from the group consisting of addition-complex type indicators, redox sensitive dye precursors and iodination type dye precursors.

11. The process of claim 10, wherein said colorimetric indicator for iodine is selected from the group consisting of soluble starch, dihydrofluorescein, o-tolidine and p-phenylenediamine.

12. A detector tube for the detection of hydrazine and volatile hydrazine derivatives in air comprising a reactor zone and an indicator zone, said reactor zone and indicator zone both being open to the atmosphere, and wherein said reactor zone contains reagents comprising an ion selected from the group consisting of iodate ion and periodate ion and wherein said indicator zone is at least partially transparent and contains a colorimetric indicator for iodine, said indicator zone further comprising an oxidizing metal ion.

13. A detector tube device for the detection of hydrazine and volatile hydrazine derivatives in air comprising a reactor zone and an indicator zone, said reactor zone being open to the atmosphere and wherein said reactor zone contains reagents comprising an ion selected from the group consisting of iodate ion and periodate ion and said indicator zone is at least partially transparent and contains a colorimetric indicator for iodine, and wherein further said indicator zone is associated with a pumping means whereby said pumping means draws air containing hydrazine or volatile hydrazine derivative into said reactor zone and draws iodine formed therein into the indicator zone where said iodine may react with the colorimetric indicator contained therein, said pumping means is a hand piston pump, and said indicator zone further comprising an oxidizing metal ion.

14. A device for the detection of hydrazine and volatile hydrazine derivatives in air comprising (1) a housing adapted to be worn on a belt and, disposed within said housing; (2) a detector tube comprising a reactor zone and an indicator zone, said reactor zone being open to the atmosphere and wherein said reactor zone contains reagents comprising an ion selected from the group consisting of iodate ion and periodate ion and said indicator zone is at least partially transparent and contains a colorimetric indicator for iodine; (3) an exhaust pump having an intake and an exhaust; (4) a conduit connecting the indicator zone of the detector tube to the intake of said exhaust pump; (5) an electric motor adapted to drive said exhaust pump; and (6) a battery for providing power to said electric motor, and wherein further said housing has a transparent window to permit observation of said detector tube, the indicator zone of said detector tube further comprising an oxidizing metal ion.

15. A detector tube for the detection of hydrazine and volatile hydrazine derivatives in air comprising a reactor zone and an indicator zone, said reactor zone and indicator zone both being open to the atmosphere, and wherein said reactor zone contains reagents comprising an ion selected from the group consisting of iodate ion and periodate ion and wherein said indicator zone is at least partially transparent and contains a colorimetric indicator for iodine, said reactor zone further comprising an oxidizing metal ion.

16. The detector tube of claim 15, wherein said detector tube has attached thereto a clip adapted to attach said detector tube to a garment.

17. The detector tube of claim 15, said indicator zone further comprising an oxidizing metal ion.

18. The detector tube of claim 17, the reagents in said reactor zone further comprising a slightly acid buffer.

19. The detector tube of claim 18, wherein the reagents in said reactor zone and the colorimetric indicator for iodine and the oxidizing metal ion in said indicator zone are on a solid support.

20. The detector tube of claim 19, wherein said solid support is selected from the group consisting of filter paper, glass beads, silica gel, pulverized fire brick, molecular sieves and polymeric granules.

21. The detector tube of claim 20, wherein said slightly acid buffer is boric acid.

22. The detector tube of claim 21, wherein said oxidizing metal ion is selected from the group consisting of cupric ion, ferric ion and mixtures thereof.

23. The detector tube of claim 22, wherein said colorimetric indicator for iodine is selected from the group consisting of addition-complex type indicators, redox sensitive dye precursors and iodination type dye precursors.

24. The detector tube of claim 23, wherein said colorimetric indicator for iodine is selected from the group consisting of soluble starch, dihydrofluorescein, o-tolidine and p-phenylenediamine.

25. The detector tube of claim 24, wherein said detector tube has attached thereto a clip adapted to attach said detector tube to a garment.

26. A detector tube device for the detection of hydrazine and volatile hydrazine derivatives in air comprising a reactor zone and an indicator zone, said reactor zone being open to the atmosphere and wherein said reactor zone contains reagents comprising an ion selected from the group consisting of iodate ion and periodate ion and said indicator zone is at least partially transparent and contains a colorimetric indicator for iodine, and wherein further said indicator zone is associated with a pumping means whereby said pumping means draws air containing hydrazine or volatile hydrazine derivative into said reactor zone and draws iodine formed therein into the indicator zone where said iodine may react with the colorimetric indicator contained therein, said pumping means is a hand piston pump, and said reactor zone further comprising an oxidizing metal ion.

27. The detector tube device of claim 26, wherein said pump is an electric pump, operating from electricity supplied by batteries.

28. The detector tube device of claim 26, said indicator zone further comprising an oxidizing metal ion.

29. The detector tube device of claim 28, the reagents in said reactor zone further comprising a slightly acid buffer.

30. The detector tube device of claim 29, wherein the reagents in said reactor zone and the colorimetric indicator for iodine and the oxidizing metal ion in said indicator zone are on a solid support.

31. The detector tube device of claim 30, wherein said solid support is selected from the group consisting of filter paper, glass beads, silica gel, pulverized fire brick, molecular sieves and polymeric granules.

32. The detector tube device of claim 31, wherein said slightly acid buffer is boric acid.

33. The detector tube device of claim 32, wherein said oxidizing metal ion as selected from the group consisting of cupric ion, ferric ion and mixtures thereof.

34. The detector tube device of claim 33, wherein said colorimetric indicator for iodine is selected from the group consisting of addition-complex type indicators, redox sensitive dye precursors and iodination type dye precursors.

35. The detector tube device of claim 34, wherein said colorimetric indicator for iodine is selected from the group consisting of soluble starch, dihydrofluorescein, o-tolidine and p-phenylenediamine.

36. A device for the detection of hydrazine and volatile hydrazine derivatives in air comprising (1) a housing adapted to be worn on a belt and, disposed within said housing; (2) a detector tube comprising a reactor zone and an indicator zone, said reactor zone being open to the atmosphere and wherein said reactor zone contains reagents comprising an ion selected from the group consisting of iodate ion and periodate ion and said indicator zone is at least partially transparent and contains a colorimetric indicator for iodine; (3) an exhaust pump having an intake and an exhaust; (4) a conduit connecting the indicator zone of the detector tube to the intake of said exhaust pump; (5) an electric motor adapted to drive said exhaust pump; and (6) a battery for providing power to said electric motor, and wherein further said housing has a transparent window to permit observation of said indicator zone wherein said transparent window is a magnifying lens, and wherein the reactor zone of said detector tube further comprises an oxidizing metal ion.

37. The device of claim 36, the indicator zone of said detector tube further comprising an oxidizing metal ion.

38. The device of claim 37, the reagents in the reactor zone of said detector tube further comprising a slightly acid buffer.

39. The device of claim 38, wherein the reagents in the reactor zone of said detector tube and the colorimetric indicator for iodine and the oxidizing metal ion in the indicator zone of said detector tube are on a solid support.

40. The device of claim 39, wherein said solid support is selected from the group consisting of filter paper, glass beads, silica gel, pulverized fire brick, molecular sieves and polymeric granules.

41. The device of claim 40, wherein said slightly acid buffer is boric acid.

42. The device of claim 41, wherein said oxidizing metal ion is selected from the group consisting of cupric ion, ferric ion and mixtures thereof.

43. The device of claim 42, wherein said colorimetric indicator for iodine is selected from the group consisting of addition-complex type indicators, redox sensitive dye precursors and iodination type dye precursors.

44. The device of claim 43, wherein said colorimetric indicator for iodine is selected from the group consisting of soluble starch, dihydrofluorescein, o-tolidine and p-phenylenediamine.

* * * * *